United States Patent [19]
Tan et al.

[11] Patent Number: 4,711,964
[45] Date of Patent: Dec. 8, 1987

[54] BISDIENE FROM BIS-BENZOCYCLOBUTENE COMPOUND

[75] Inventors: Loon-Seng Tan; Fred E. Arnold, both of Centerville, Ohio

[73] Assignee: University of Dayton, Dayton, Ohio

[21] Appl. No.: 861,020

[22] Filed: May 8, 1986

[51] Int. Cl.$^4$ ............................................ C07D 209/48
[52] U.S. Cl. ..................................... 548/461; 528/170; 528/220; 528/321; 528/322; 548/474; 548/480; 548/513; 548/545; 548/546; 548/547; 548/520
[58] Field of Search .............. 548/545, 461, 474, 480, 548/513, 546, 547; 528/322

[56] References Cited

U.S. PATENT DOCUMENTS 4,540,763 9/1985 Kirchhoff .
4,570,011 3/1986 So .

FOREIGN PATENT DOCUMENTS

86/100718.5 9/1986 European Pat. Off. .

Primary Examiner—Harold D. Anderson
Attorney, Agent, or Firm—Biebel, French & Nauman

[57] ABSTRACT

Resins are prepared by polymerization of compounds of the formula

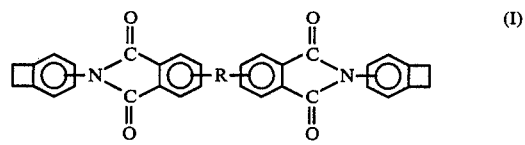

where R is a divalent linking group.

Blends of a compound of the formula (I) as defined above and a bis-maleimide of the formula

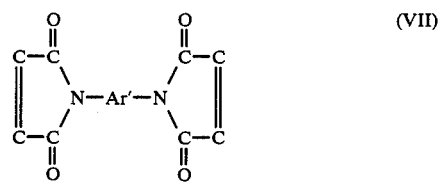

where Ar' is an aromatic linking group.

10 Claims, 5 Drawing Figures

FIG. 1 DSC of

FIG-3

FIG-5 ISOTHERMAL AGING (AIR, 650°F, 200 HRS)

BISDIENE FROM BIS-BENZOCYCLOBUTENE COMPOUND

The U.S. Government has rights in this invention pursuant to Contract No. F33615-84-C-5020 awarded by the Department of the Air Force.

BACKGROUND OF THE INVENTION

The present invention relates to resins obtained by polymerization of compounds, and more particularly, to high temperature resistant thermoset resins obtained by polymerization of bis-benzocyclobutene compounds.

One form of a cycloaddition reaction is the Diels-Alder reaction in which an unsaturated group, a dienophile, combines with a 1,3-diene to form a six membered ring. Benzocyclobutene functions very well in a Diels-Alder reaction. As taught by W. Oppolzer, *Synthesis* 793 (1978), under appropriate thermal conditions, the benzocyclobutene unit undergoes an electrocyclic ring opening to form the more reactive o-xylylene functionality. O-xylylene is a powerful diene, and thus, engages in a Diels-Alder reaction in the presence of a suitable dienophile. See Boekelheide, *Accounts Chem. Res.* 13, 65 (1980).

An example of a suitable dienophile is a bis-maleimide. Bis-maleimides are well-known as possessing strong dienophilicity. The dienophilic site, i.e., the carbon-carbon double bond, is not subjected to the substituent effect imposed by the rest of the structure. Thus, a bis-maleimide engages in a Diels-Alder polymerization in the presence of a suitable bisdiene such as bis (o-xylylene).

In the absence of a suitable dienophile, benzocyclobutene will react with itself. Although the exact cure mechanism for the bis-benzocyclobutene systems is still unclear, the results of studies in F. Jensen, W. Coleman, and A. Berlin, *Tet. Lett.* 15 (1962) and L. Errede, *J. Am. Chem. Soc.* 83, 949 (1961) suggest that at least two possible pathways exist: (1) cycloaddition and (2) linear addition. In the cycloaddition mode, an eight member ring is formed and incorporated into the highly aromatic skeleton. However, in the linear addition mode, a polymeric structure with a double strand of poly (o-xylylene) bridged by the aromatic imide groups results. It should be noted, however, that the terms "cycloaddition" and "linear addition" are used to describe the polymeric structures and do not implicate the mechanisms from which they arise.

Bis-benzocyclobutenes and polymers derived therefrom are disclosed in U.S. Pat. No. 4,540,763. The bis-benzocyclobutenes are connected by direct bond or a bridging member such as a cyclic imido group. In general, the polymers are obtained by addition polymerization wherein the fused cyclobutene rings undergo thermal transformation to o-xylylene moieties which can react with one another.

SUMMARY OF THE INVENTION

An object of the present invention is to provide compounds useful in the preparation of high temperature resistant thermoset resins.

A more particular object of the present invention is to provide high temperature resistant thermoset resins prepared by polymerization of bis-benzocyclobutene imide compounds.

An additional object of the present invention is to provide high temperature resistant thermoset resins which are useful in composite materials in the advanced aircraft and aerospace vehicles.

A further object of the present invention is to provide compounds which are polymerizable by Diels-Alder polymerization.

Another object of the present invention is to provide high temperature resistant thermoset resins prepared by Diels-Alder polymerization of bis-benzocyclobutene imide compounds with bis-maleimides.

The present invention provides compounds of the general formula where R is a divalent linking group. Upon heating these compounds to about 200° C., the benzocyclobutene unit undergoes an electrocyclic ring-opening to form the more reactive o-xylylene functionality which is a powerful diene.

In accordance with the present invention, when suitable bis-dienophiles are present, resins are obtained by Diels-Alder polymerization of bis-benzocyclobutene imide compounds with the bis-dienophiles. When suitable bis-dienophiles are absent, resins are obtained by the cycloaddition or linear addition polymerization of the bis-benzocyclobutene imide compounds with themselves. In the cycloaddition mode, an eight membered ring forms and is incorporated into the highly aromatic skeleton. In the linear addition mode, a polymeric structure with a double strand of poly (o-xylylene) bridged by the aromatic imide groups results.

In one embodiment, the compound is represented by the formula (Ia)

where R is a divalent linking group.

In the compound of formula (I) above, careful attention must be paid to the selection of the R-moiety. R is selected so as to maximize the thermooxidative stability of the resin. Isothermal aging studies indicate that as the structural rigidity of the R-moiety increases, the thermooxidative stability of the R-moiety increases. For example, when R is selected from the group consisting of the following, the increasing order of thermooxidative stability is Thus, in a preferred embodiment, R is a perfluoro-aliphatic group such as —C(CF$_3$)$_2$—. In another embodiment, R is an aromatic linking group. In other applications where thermooxidative stability is not as critical, numerous R groups are useful in the compounds of the present invention.

In one embodiment, R is selected from the group consisting of —C(CH$_3$)$_2$—, —CH$_2$—, —O—, —S—, —CO—, —SO$_2$—, and a direct bond.

In another embodiment, R is represented by the formula (II)

(II)

where W is selected from the group consisting of —C(CF$_3$)$_2$—, —C(CH$_3$)$_2$—, —CH$_2$—, —O—, —S—, —CO—, —SO$_2$—, and a direct bond.

In a more particular embodiment, R is represented by the formula (IIa)

(IIa)

where W is as defined above.

In another embodiment, R is represented by the formula (III)

(III)

where X is selected from the group consisting of —C(CF$_3$)$_2$—, —C(CH$_3$)$_2$—, —CH$_2$—, —O—, —S—, —CO—, —SO$_2$—, and a direct bond.

In a more particular embodiment, R is represented by the formula (IIIa)

(IIIa)

where X is as defined above.

In an additional embodiment, R is represented by the formula (IV)

(IV)

where
R' is selected from the group consisting of —C(CF$_3$)$_2$—, —C(CH$_3$)$_2$—, —CH$_2$—, —O—, —S—, —CO—, —SO$_2$—, and a direct bond,
n is 1 to 4, and
Ar is an aromatic linking group such as a linking group selected from the group consisting of a meta phenylene group, a para phenylene group, and the formula (III) as defined above.

In accordance with the present invention, when suitable bis-dienophiles are present, resins are obtained by Diels-Alder polymerization of the bis-benzocyclobutene imide compounds with the bis-dienophiles. A suitable bis-dienophile is a bis-maleimide. Thus, the present invention also provides blends of the aforementioned bis-benzocyclobutenes and bis-maleimides of the formula (VII)

(VII)

where Ar' is an aromatic linking group.

In one embodiment, Ar' is an aromatic linking group such as a linking group selected from the group consisting of a meta phenylene group, a para phenylene group and the formula (III)

(III)

where X is selected from the group consisting of —C(CF$_3$)$_2$—, —C(CH$_3$)$_2$—, —CH$_2$—, —O—, —S—, —CO—, —SO$_2$—, and a direct bond.

Aromatic ether bis-maleimides are also useful as dienophiles in the present invention.

Other objects and advantages of the invention will be apparent from the following description, the accompanying drawings and the appended claims.

DETAILED DESCRIPTION OF THE INVENTION

Bis-benzocyclobutene imide compounds useful in the present invention can be prepared by several synthesis schemes. In general, the compounds of the present invention are prepared by condensing 4-aminobenzocyclobutene with a dianhydride.

The following reaction scheme sets forth the synthesis of 4-aminobenzocyclobutene.

of 1,4-bis(3,4-dicarboxyphenoxy) diphenylsulfone dianhydride (BSDA).

Step (A) is explained in Cava and Napier, *J. Am. Chem. Soc.* 79, 1701 (1957). Sanders and Giering, *J. Org. Chem.* 38, 3055 (1973) provides details on Step (B). Step The following reaction scheme sets forth the general synthesis of certain bis-benzocyclobutene imides useful in the present invention.

(C) is discussed in Lloyd and Ongley, *Tetrahedron* 20, 2185 (1964) while Step (D) is discussed in Horner and Schmelzer, *Chem Ber* 93, 1774 (1960).

The dianhydrides useful in preparing the compounds of the present invention are prepared in a conventional manner. For example, U.S. Pat. No. 4,196,277 discloses the preparation of 2,2-bis[4-(3,4-dicarboxyphenoxy) phenyl] hexafluoropropane dianhydride (BFDA). Similarly, U.S. Pat. No. 3,812,159 discloses the preparation The preferred methods of preparation of certain bis-benzocyclobutene imides useful in the present invention are described in the Examples below.

In the absence of a suitable dienophile, the compound reacts with itself. Although the exact cure mechanism is unclear, studies suggest that at least two possible pathways exist: 1) cycloaddition and 2) linear addition.

Following the cycloaddition mode, a polymer including an eight membered ring of the formula (V)

(V)

is believed to form where n is greater than or equal to 10 and is incorporated into the highly aromatic skeleton. In general, cycloaddition polymerization of the compounds occurs at a temperature of greater than about 200° C.

Following the linear addition mode, a polymeric structure of the formula (VI)

(VI)

with a double strand of poly (o-xylylene) bridged by the aromatic imide groups is believed to result where n is greater than or equal to 10. In general, linear addition of the compounds occurs at a temperature of greater than about 200° C. The terms "cycloaddition" and "linear addition" are used to describe the structures and do not implicate the mechanisms from which they arise.

Figure 1:
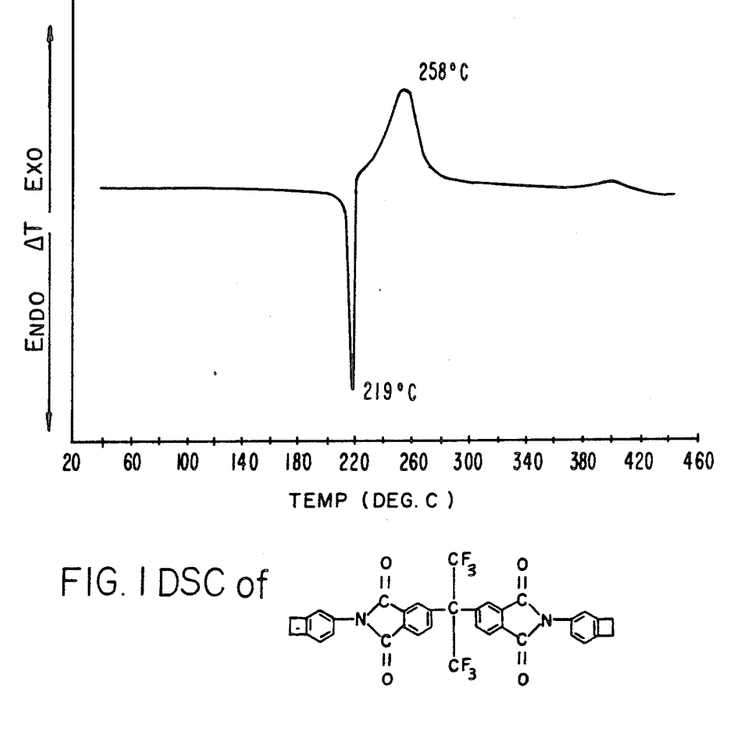
FIG. 1 is a DSC (differential scanning calorimetry) curve of bis-2,2-(N-4-benzocyclobutenyl phthalimido) hexafluoropropane.

A differential Scanning Calorimetric (DSC) study indicates the endothermic or exothermic nature of a reaction as the temperature increases. Typically, the reaction temperature is plotted on the abscissa while the temperature change is plotted on the ordinate. A DSC study is useful in the prsent invention because it indicates the exotherms for a given compound. For example, when R is $-C(CF_3)_2-$ in the compound of formula (Ia) above, the DSC is represented by FIG. 1 which was run at a heating rate of 10° C. per minute. FIG. 1 shows a melting temperature of about 219° C. and a reaction exotherm of 258° C.

Table 1 sets forth thermal properties of compounds of formula (Ia).

TABLE 1

THERMAL PROPERTIES OF COMPOUNDS OF FORMULA (Ia)

| Examples | $T_g$ | $T_m$ | $T_{poly}$ ONSET | $T_{poly}$ MAX | $T_g$(CURE) DSC | ISOTHERMAL AGING 200 HRS/AIR % WEIGHT LOSS |
|---|---|---|---|---|---|---|
| 1 | 116 | 219 | 230 | 258 | 281 | 9% (600° F.) |
|   |     |     |     | 404 |     | 13% (650° F.) |
|   |     |     |     |     |     | 40% (700° F.) |
| 2 | 62  | —   | 229 | 263 | 247 | 7% (600° F.) |
|   |     |     |     | 369 | (251) (TMA) | 25% (650° F.) |
|   |     |     | 250 | 263 |     |     |
| 3 | 149 | 249 |     | 357; | 240 | 10% (600° F.) |
|   |     |     |     | 377 |     |     |

All Table 1 temperature values are expressed in °C. unless otherwise specified. The Example numbers correspond to the examples given below. Tg is the glass transition temperature of the compound while Tm is the melting temperature of the compound. Tpoly onset is the beginning polymerization temperature while Tpoly max is the temperature at which polymerization reaches its maximum. The second Tpoly max values represent small, secondary exotherms which were observed for both cured and uncured samples. Tg(cure) is the glass transition temperature of the polymer; the Tg(cure) measurements were made on samples previously cured under N₂ atmosphere at 250°-254° C. for 8 hours. TMA means determined by thermal mechanical analysis. The isothermal aging studies were carried out in circulating air for 200 hours at constant temperature as specified.

Figure 2:
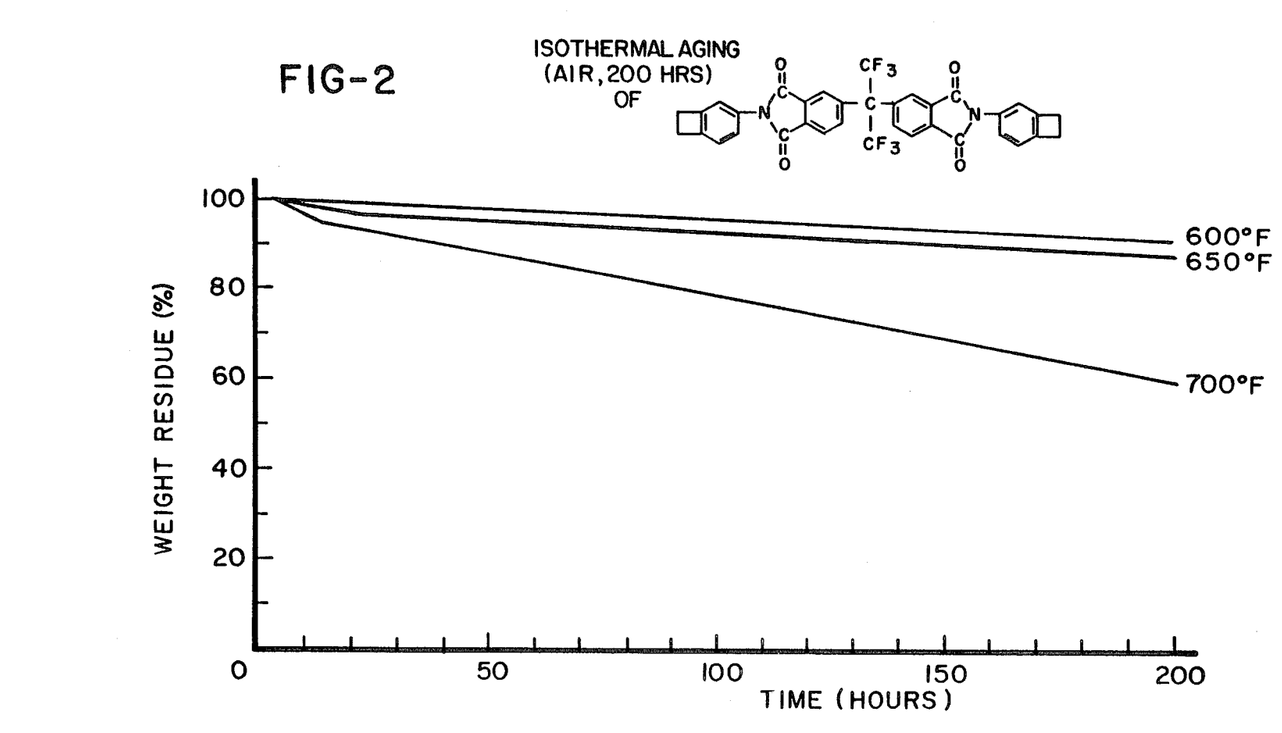
FIG. 2 provides isothermal aging studies for bis-2,2-(N-4-benzocyclobutenyl phthalimido) hexafluoropropane.

FIG. 2 represents isothermal aging studies of bis-2,2-(N-4-benzocyclobutenyl phthalimido) hexafluoropropane. The samples were cured as indicated above for Tg(cure). The isothermal aging studies were carried out by placing cured samples in a circulating air oven for 200 hours, and periodically measuring the change in weight. This data illustrates the high temperature utility of the compounds.

Table 2 sets forth thermal characteristics of compounds of formula (Ia) where R is represented by formula (IV) and R' is $-C(CF_3)_2-$.

TABLE 2

THERMAL CHARACTERISTICS OF COMPOUNDS OF FORMULA (Ia) WHERE R IS REPRESENTED BY FORMULA (IV) AND R' IS —C(CF$_3$)$_2$—

| Examples | T$_g$ | T$_m$ | Curing Exotherm ONSET | Curing Exotherm MAX | T$_g$(CURE) | T$_{10\%}$ | ISOTHERMAL AGING 200 HR/AIR % WEIGHT LOSS |
|---|---|---|---|---|---|---|---|
| 1 | 116 | 219 | 232 | 258 | 281 | 496 | 43% (700° F.) |
| 4 | 81 | — | 197 | 257 | 258 | 470 | 12% (650° F.) |
|   |    |   |     |     | 256 (DSC) |   | 43% (700° F.) |
|   |    |   |     |     | 288 |   |   |
| 7 | 81 | — | 210 | 254 | 314 (TMA) | 500 | 12% (650° F.) |
|   |    |   |     |     | 299 (DSC) |   | 24% (700° F.) |
| 6 | 78 | — | 208 | 254 | 289 (DSC) | 519 | 35% (700° F.) |
| 5 | 81 | — | 213 | 252 | 282 (DSC) | 518 | 41% (700° F.) |

All Table 2 temperature values are expressed in °C. unless otherwise specified. The Example numbers correspond to the examples given below. Tg is the glass transition temperature of the compound while Tm is the melting temperature of the compound. Curing exotherm onset is the beginning cure temperature while curing exotherm max is the maximum cure temperature. Also, small exotherms around 360°-380° C. were observed. Tg(cure) is the glass transition temperature of the polymer. The Tg(cure) values without (DSC) following were obtained by rescanning samples previously heated to 450° C. on a DSC; the Tg(cure) values with (DSC) or (TMA) following were obtained from samples previously cured at 250° C./8 hours/N$_2$. TMA means determined by thermal mechanical analysis. T$_{10\%}$ is the temperature at which a 10% weight loss of the sample was determined by thermal gravimetric analysis (TGA). The isothermal aging studies were carried out in circulating air for 200 hours at the temperature specified.

The cure mechanism for the bis-benzocyclobutene systems has a significant impact on the nature and properties of the resins prepared. In a preferred embodiment, the resins are useful in composite materials in the advanced aircraft and aerospace vehicles.

The resins of the present invention can be prepared by Diels-Alder polymerization of the particular compounds used if suitable dienophiles are present. Upon heating the compounds to 200° C., Diels-Alder polymerization occurs whereby the benzocyclobutene unit undergoes an electrocyclic ring opening to form the more reactive o-xylylene functionality wherein the o-xylylene functionality undergoes cycloaddition with the dienophile.

In general, Diels-Alder polymerization of the compounds occurs at a temperature of greater than about 200° C.

Dienophiles suitable for use in a Diels-Alder reaction are useful in the present invention. Examples of useful dienophiles include benzoquinones, bis-maleimides, and cyclopentadienes. Preferred dienophiles are bis-maleimides.

Bis-maleimides useful in the present invention can be prepared using fully conventional methods. The classic imidization reaction can be employed. For example, maleic anhydride can be reacted with the diamine corresponding to the final product bis-maleimide desired. Typically, the imidization is carried out in an inert aprotic solvent such as dimethylformamide, dimethylsulfoxide, or acetamide using a slight excess of maleic anhydride. Typical reaction temperatures are 40°-60° C. Typical reaction times are 1-1.5 hours.

Aromatic ether bis-maleimides are also useful in the present invention. As taught in U.S. Pat. No. 4,460,783, an ether imide can be prepared in a two step reaction. First, a diamine is contacted with an ethylenically unsaturated dicarboxylic acid anhydride in an organic solvent at a temperature of −10° to +40° C. for 0.5-10 hours to give an ether amic acid. Second, the ether amic acid is subjected to ring closing dehydration to form imide rings. U.S. Pat. No. 4,460,783 is incorporated here by reference.

The following scheme sets forth the possible polymerization reactions of maleimide.

POLYMERIZATION REACTIONS OF MALEIMIDE

As the scheme indicates, the maleimine functionality can react with a variety of nitrogen or sulfur nucleophiles in Michael-Addition fashion. Such an addition reaction is, in fact, the chemical basis of kerimide and related thermosetting resins. The maleimide functionality is also capable of homopolymerization. The maleimide functionality is also well-known to possess dienophilicity. The dienophilic site, i.e., the carbon-carbon double bond, is not subjected to the substituent effect imposed by the rest of the structure. The maleimide functionality is ideal for Diels-Alder polymerization.

The present invention provides resin blends of compounds of the formula (I) with bis-maleimides of the formula (VII) which are useful in providing reaction products by Diels-Alder polymerization. Upon heating the bis-benzocyclobutene compounds to about 200° C., Diels-Alder polymerization occurs whereby the benzocyclobutene unit undergoes an electrocyclic ring-opening to form the more reactive o-xylylene functionality wherein the o-xylylene functionality undergoes cycloaddition with the maleimide functionality. Homopolymerization of the maleimide functionality and the bis-benzocyclobutene functionality can occur simultaneously with the Diels-Alder polymerization. However, in preparing the resins, the Diels-Alder polymerization should occur at a substantially greater rate than the homopolymerization of the maleimide functionality or the bis-benzocyclobutene functionality in order to maximize the thermal stability of the resins. In general, Diels-Alder polymerization occurs at a temperature of about 200° to 250° C. while homopolymerization occurs at a temperature of about 185° to 240° C.

The resultant resin can be aromatized at high-temperature in the presence of air ($O_2$) to enhance the thermodynamic stability of the final polymeric structure. Although gaseous $H_2O$ will be produced as a volatile by-product, such process will take place primarily on the surface of the thermosets and the adverse effect due to void-formation will be minimal.

Figure 3:
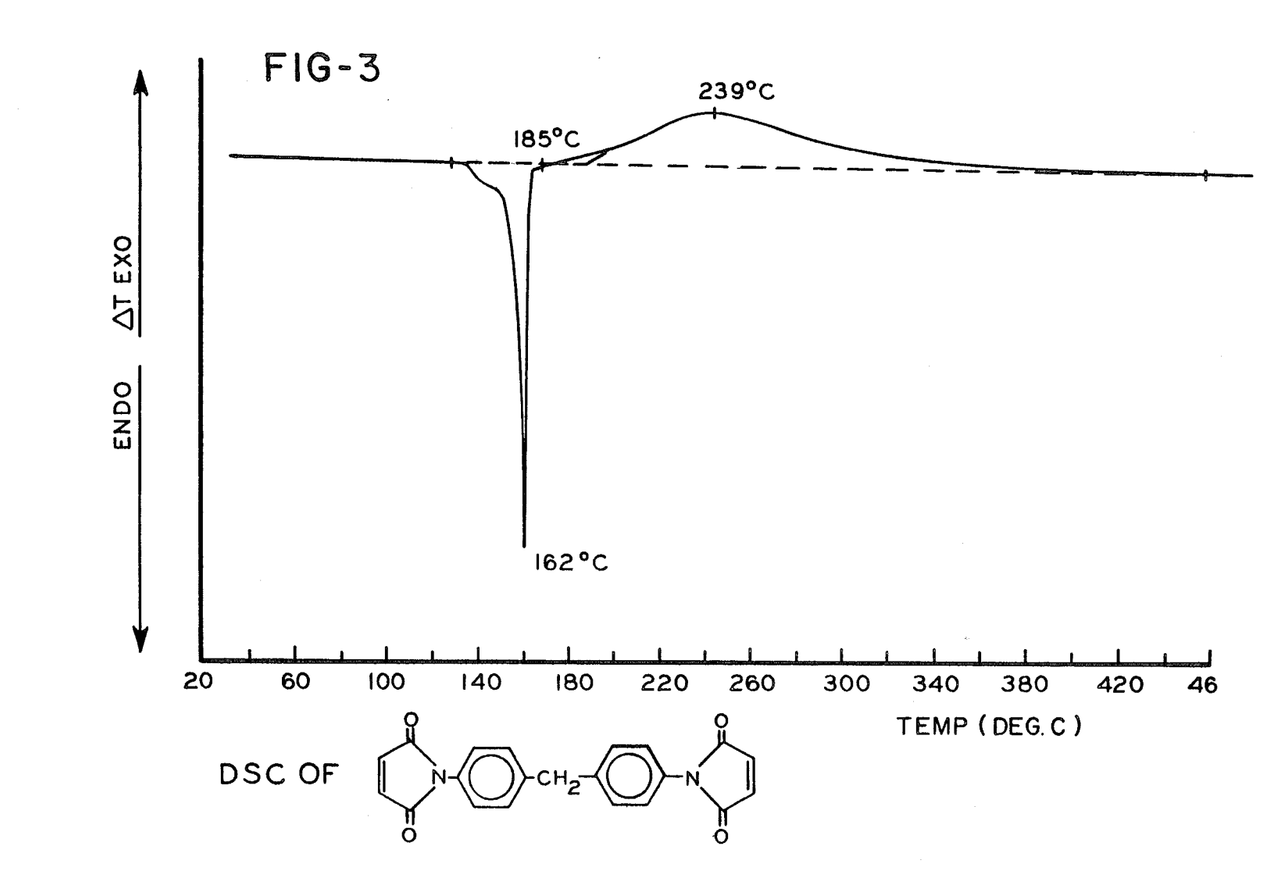
FIG. 3 is a DSC of 1,1'-(methylene di-4,1-phenylene)-bis-maleimide.

FIG. 3 is a DSC of 1,1'-(methylene di-4,1 phenylene)-bis-maleimide. The scan rate was 10° C. per minute. FIG. 3 shows a melting temperature of about 162° C. and a reaction exotherm of about 239° C.

Figure 4:
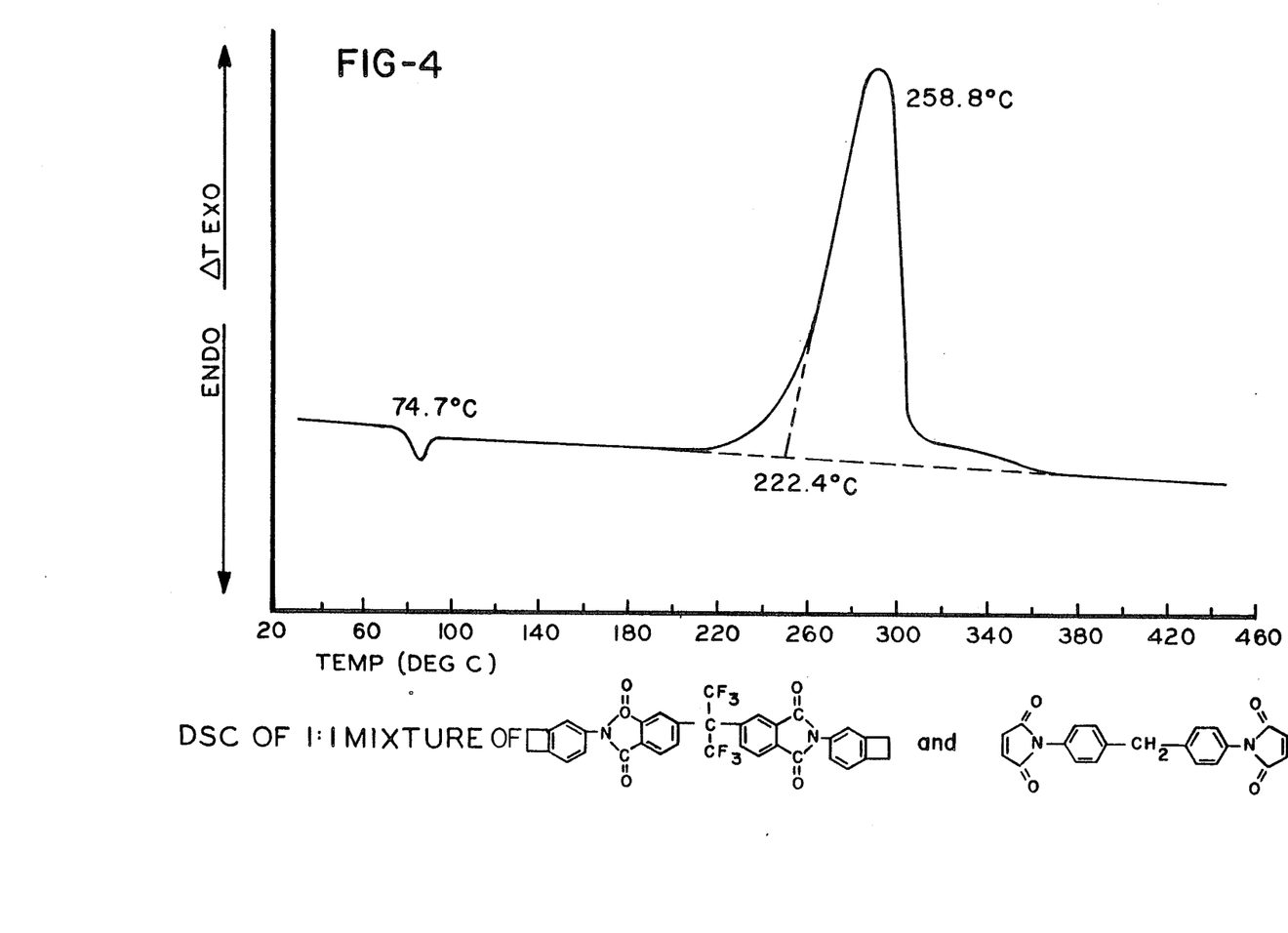
FIG. 4 is a DSC of a resin which is a reaction product prepared by Diels-Alder polymerization of a 1:1 molar ratio of bis-2,2-(N-4-benzocyclobutenyl phthalimido) hexafluoropropane with 1,1'-(methylene di-4,1-phenylene)bis-maleimide.

FIG. 4 is a DSC of a 1:1 molar ratio mixture of bis-2,2-(N-4-benzocyclobutenyl phthalimido) hexafluoropropane and 1,1-(methylene di-4,1-phenylene)bis-maleimide. FIG. 4 shows a Tpoly max of about 259° C. The complete compatibility is evidenced by a single Tg. At about 259° C., Diels-Alder polymerization predominates over homopolymerization of the maleimide or bis-benzocyclobutene functionality because the reaction sites are much more reactive toward Diels-Alder polymerization than homopolymerization. The Diels-Alder polymerization occurs at a substantially faster rate so that the Diels-Alder polymerization product is favored.

Table 3 sets forth thermal properties of compatible mixtures of bis-2,2-(N-4-benzocyclobutenyl phthalimido) hexafluoropropane (BCB) and 1,1'-(methylene di-4,1-phenylene) bis-maleimide (BMI).

TABLE 3

THERMAL CHARACTERISTICS OF COMPATIBLE MIXTURES OF BIS-2,2-(N—4-BENZOCYCLOBUTENYL PHTHALIMIDO) HEXAFLUOROPROPANE (BCB) AND 1,1'-(METHYLENE DI-4,1-PHENYLENE) BIS-MALEIMIDE (BMI)

| MOLAR RATIO | | | | $T_{poly}$ | | | |
|---|---|---|---|---|---|---|---|
| BCB | BMI | $T_{g(ini)}$ | $T_m$ | Onset | Max. | $T_g$(cure) | $T_{10\%}$(Air) |
| 1 | 0 | 116 | 219 | 232 | 258 | 281[b] | 496 |
| 0 | 1 | — | 162 | 185 | 239 | —[c] | 492 |
| 1 | 1 | 61 | — | 224 | 259 | 293[a] | 500 |
| 1 | 1.5 | 68 | — | 221 | 257 | 298[a] | 520 |

TABLE 3-continued

THERMAL CHARACTERISTICS OF COMPATIBLE MIXTURES OF BIS-2,2-(N—4-BENZOCYCLOBUTENYL PHTHALIMIDO) HEXAFLUOROPROPANE (BCB) AND 1,1'-(METHYLENE DI-4,1-PHENYLENE) BIS-MALEIMIDE (BMI)

| MOLAR RATIO | | | | $T_{poly}$ | | | |
|---|---|---|---|---|---|---|---|
| BCB | BMI | $T_{g(ini)}$ | $T_m$ | Onset | Max. | $T_g$(cure) | $T_{10\%}$(Air) |
| 1 | 3 | 70 | — | 225 | 257 | —[c] | 492 |
| 1.5 | 1 | 68 | — | 222 | 257 | 298[a] | 515 |

All Table 3 temperature values are expressed in ° C. Tg(ini) is the initial glass transition temperature while Tm is the melting temperature. Tpoly onset is the beginning polymerization temperature while Tpoly max is the temperature at which polymerization reaches its maximum. Tg(cure) is the glass transition temperature of the cured mixture. Tg(cure) was determined by both DSC analysis (value a) and by thermomechanical analysis (value b) which employ a sensitive probe to detect the softening of the sample at its surface. Value c indicates that Tg(cure) was not observed by DSC. Because Tg(cure) relates to the cured material, all samples were cured at 250° C. under $N_2$ atmosphere for 8 hours. $T_{10\%}$ air is the temperature at which a 10% weight loss was observed by thermal gravimetric analysis.

Figure 5:
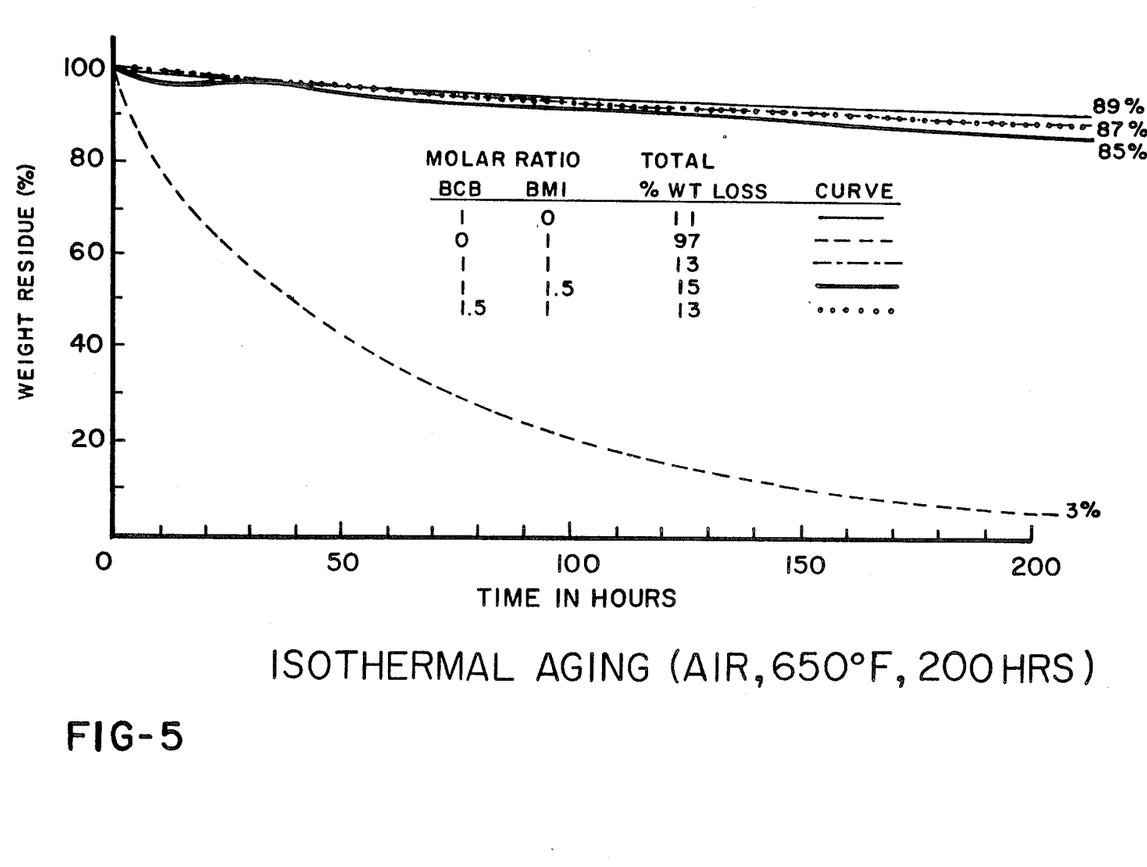
FIG. 5 provides isothermal aging studies for bis-2,2-(N-4-benzocyclobutenyl phthalimido) hexafluoropropane; 1,1'-(methylene di-4,1-phenylene)bis-maleimide; and resins prepared by Diels-Alder polymerization of different molar ratios thereof.

FIG. 5 represents isothermal aging studies of cured mixtures of BCB and BMI. The samples were cured as indicated above for Tg(cure). The isothermal aging studies were carried out by placing cured samples in a circulating air oven at 343° C. for 200 hours, and periodically measuring the change in weight. The cured BMI sample was almost completely vaporized whereas all mixtures exhibited similar thermooxidative stabilities to BCB. This data illustrates the high temperature utility of the resins.

The cure mechanism for the bis-benzocyclobutene bis-maleimide systems has a significant impact on the nature and properties of the resins prepared. In a preferred embodiment, the resins are useful in composite materials in the advanced aircraft and aerospace vehicles.

The present invention is illustrated in more detail by the following non-limiting Examples.

EXAMPLE 1

Preparation of bis-2-2-(N-4-benzocyclobutenyl phthalimido) hexafluoropropane

A mixture of bis-2,2-(4-phthalic anhydrido) hexafluoropropane (4.00 g, 10.1 mmol) and 4-aminobenzocyclobutene (2.40 g, 20.1 mmol) freshly prepared from the catalytic hydrogenation of 4-nitrobenzocyclobutene, were gently refluxed in acetic acid (75 ml) under nitrogen atmosphere overnight. The resultant dark and homogeneous reaction mixture was allowed to cool to room temperature and poured into 300 ml of $H_2O$. Immediately, precipitation of gray solids occurred, which could be extracted into ethyl ether (100 ml., then 3X50 ml). The ethereal extract was then washed with aqueous sodium carbonate and dried over magnesium sulfate. Subsequent removal of the solvent by rotary evaporation led to the isolation of about 5.5 g of crude dark brown product, which was subjected to the following chromatographic purification. The crude product was dissolved in about 20 ml of methylene chloride and added to a quartz column (internal diameter: 2.0 cm)

containing about 120 g of silica gel and saturated with petroleum ether. Elution with 1:1 ether/petroleum ether resulted in the collection of light yellow solution as first fractions, which upon standing at room temperature, gradually deposited light yellow needles. The product was collected, washed with petroleum ether and dried in an oven at 100° C. for about an hour. Yield: 3.78 g (57.8%). mp=216°-216.5° C. Calc. for $C_{35}H_{20}F_6N_2O_4$: 65.02 % C; 3.12% H; 4.33% N. Found: 65.07% C; 3.23% H; 4.18% N. Mass spectroscopy: M/e=646 (M+) 30.7%. Proton NMR (CDCl$_3$): 3.26 (singlet, alicyclic protons): 7.07-7.30, 7.85-8.18 (complex, aromatic protons). IR (KBr Pellet): 2968 W, 2925 W (alicyclic C-H stretches); 1778 M, 1717 vs (imide group stretches); 1243 s, 1188 s (asymmetric and symmetric stretches of —C(CF$_3$)$_2$- group).

EXAMPLE 2

Preparation of 2,2-bis [4(N-4'-benzocyclobutenyl-4"-phenoxyphthalimido)] hexafluoropropane A mixture of 1.63 g (13.7 mmol) of freshly prepared 4-aminobenzocyclobutene and 4.00 g (6.36 mmol) of 2,2-bis[4-(3,4-dicarboxyphenoxy) phenyl] hexafluoropropane dianhydride (BFDA) was heated to reflux in acetic acid (60ml) under N$_2$. The reaction mixture became homogeneous and dark upon reflux, which was maintained for about 17 hrs. The dark reaction mixture was allowed to cool to room temperature and poured into about 350 ml of distilled water. Extraction was subsequently conducted using methylene chloride (100 ml, then 3×50 ml) as the extracting solvent. The organic extract was then washed with aqueous sodium carbonate and saturated sodium chloride solution, and finally dried over magnesium sulfate. The resultant solution was concentrated on a rotary evaporator until its volume was about 50 ml, and subjected to chromatographic purification. (350 g silica gel saturated with hexane; 1:1 CH$_2$Cl$_2$/hexane as eluent.) The desired product was obtained, after the removal of solvent from the first fractions, as light yellow microcrystalline solid. Yield: 3.74 g (67.8%). mp=128°-132° C. Calc. for $C_{47}H_{28}F_6O_6N_2$: 67.94% C; 3.40% H; 3.37% N. Found: 67.99% C; 3.76 H; 3.19% N. Mass spectroscopy: 830 (M+, 2%); 415 (M++, 6%). Proton NMR (CDCl$_3$): 3.23 (singlet, alicyclic protons); 7.06-8.03 (complex, aromatic protons). IR (KBr pellet): 2922 W, 2960 VW (alicyclic C—H stretches); 1714 vs, 1771 m (imide group stretches); 1202 m, 1235 s (symmetric and asymmetric stretches of —C(CF$_3$)$_2$—group); 1168 ms (Ar—O—Ar stretch).

EXAMPLE 3

Preparation of bis[4(N-4'-benzocyclobutenyl-4"-phenoxyphthalimido)] Sulfone

A mixture of 4-aminobenzocyclobutene (0.75 g, 6.29 mmol) and 1,4-bis(3,4-dicarboxyphenoxy) diphenylsulfone dianhydride (BSDA) (1.50 g, 2.96 mmol) was refluxed in acetic acid (55 ml) under N$_2$ overnight. The resultant dark reaction mixture was allowed to cool to room temperature and poured into 300 ml of distilled water. The crude product was then extracted into methylene chloride (100 ml, then 3×50 ml) and the organic extract was subsequently treated with aqueous 10% sodium bicarbonate and saturated sodium chloride solution. After having been dried over magnesium sulfate, the methylene chloride extract was concentrated on a rotary evaporator until its volume was about 35-40 ml. Subsequent chromatographic purification (300 g silica gel saturated with petroleum ether; 1:1 methylene chloride/petroleum ether as the eluting solvent) led to the isolation of the desired product, which was obtained from the first fractions as light yellow microcrystalline solid. Yield: 1.18 g (53.6%). mp=245°-246° C. Calc. for $C_{44}H_{28}N_2O_8S$: 70.96% C; 3.79% H; 3.76% N. Found: 70.81% C; 3.99% H; 3.64% N. Proton NMR (CDCl$_3$): 3.25 (singlet, alicyclic protons); 7.09-7.54, 7.96-8.16 (complex, aromatic protons). IR (KBr pellet): 3060 VW, 3085 VW (aromatic C—H stretches); 2930 W, 2965 VW (alicyclic C-H stretches); 1700 VS; 1764 ms (imide group stretches); 1232 VS, 1372 VS (symmetric and asymmetric stretches of —SO$_2$— group); 1089 ms, 1102 ms (Ar—O—Ar stretches).

EXAMPLE 4

Compound prepared from bis-2,2-(4-phthalic anhydrido) hexafluoropropane; 2,2'-bis(3-aminophenyl)hexafluoropropane; and 4-aminobenzocyclobutene 4.08 g (9.18 mmol) of bis-2,2-(4-phthalic anhydrido) hexafluoropropane suspended under N$_2$ in acetic acid (100 ml)/toluene (80 ml) was heated to about 65° C., at which temperature all the dianhydride dissolved. 2,2'-bis(3-aminophenyl) hexafluoropropane (1.50 g. 4.49 mmol) was subsequently added neat in small portions over a period of 20 minutes, at which the temperature of the reaction mixture was maintained at 70°-80° C. The resultant yellow homogeneous reaction mixture was then heated to reflux and the water of condensation was collected azeotropically. After an overnight reflux, the yellow reaction was allowed to cool to about 40° C. and freshly prepared 4-aminobenzocyclobutene (2.80 g, 23.5 mmol) in about 10 ml of toluene was added. Reflux of the reaction mixture was resumed and continued for another 30 hrs under N$_2$. The dark reaction mixture was allowed to cool to room temperature and poured into 600 ml of distilled water. Extraction was performed using ethyl acetate as the extracting solvent (100 ml, then 3×50 ml). The organic extract was then washed with 10% aqueous sodium bicarbonate (500 ml) and then distilled water (2×500 ml). After having dried over magnesium sulfate, the organic extract was subjected to rotary evaporation to remove all the solvent. The fluffy gray crude product was then dissolved in methylene chloride and the resultant solution was filtered through a bed of silica gel (40 g), washing with methylene chloride until the filtrate was almost colorless. The yellow filtrate was rota-evaporated to remove about half the volume of the solvent. Hexane was added to gradually precipitate out light tan microcrystalline solid. The solvents were further removed and the product was finally collected, washed with hexane, and dried in vacuo at approximately 60° C. for two days. Yield=7.60 g.

Another batch of the oligomer was prepared similarly except for the purification step. Thus, 5.75 g (12.94 mmol) of bis-2,2-(4-phthalic anhydrido) hexafluoropropane, 2.06 g (6.16 mmol) of 2,2-bis(3-aminophenyl) hexafluoropropane and 3.84 g (32.23 mmol) of 4-aminobenzocyclobutene were reacted in 150 ml acetic acid/200 ml toluene mixture. After the usual work-up as described above, the crude product was dissolved in a minimal amount of methylene chloride and the resultant solution was passed through a small column containing about 20 g of silica gel. The column was then eluted with methylene chloride until all fluorescent material was collected. Removal of the solvents from the fractions collected led to the isolation of 8.04 g of yellow microcrystalline solid as the pure product.

EXAMPLE 5

Compound prepared from bis-2,2-(4-phthalic anhydrido) hexafluoropropane oxydianiline and 4-aminobenzocyclobutene.

5.75 g (12.94 mmol) of bis-2,2-(4-phthalic anhydrido) hexafluoropropane, 1.30 g (6.49 mmol) of oxydianiline and 3.70 g (31.0 mmol) of 4-aminobenzocyclobutene were reacted in 200 ml acetic acid/100 ml toluene. The crude product was dissolved in approximately 100 ml methylene chloride, after the usual work-ups as described above. The resultant solution was then passed through a small column containing about 50 g silica gel, using hexane as the eluting solvent. The desired product was obtained from the first fractions as amber microcrystalline solid. Yield: 6.40 g.

EXAMPLE 6

Compound prepared from bis-2,2-(4-phthalic anhydrido) hexafluoropropane p-phenylenediamine and 4-aminobenzocyclobutene.

5.75 g (12.94 mmol) of bis-2,2-(4-phthalic anhydrido) hexafluoropropane, 0.80 g (7.40 mmol) of p-phenylenediamine and 3.60 g (30.21 mmol) of 4-aminobenzocyclobutene were reacted in 200 ml acetic acid/100 ml toluene. The crude product was dissolved in about 30 ml of methylene chloride and the resultant solution was passed through a small column containing 50 g of silica gel saturated with petroleum ether, which was also used as the eluting solvent. The desired product was a golden microcrystalline solid. Yield: 4.60 g.

EXAMPLE 7

Compound prepared from bis-2,2-(4-phthalic anhydrido) hexafluoropropane; m-phenylenediamine; and 4-aminobenzocyclobutene 3.79 g (8.53 mmol) of bis-2,2-(4-phthalic anhydrido) hexafluoropropane, 0.45 g (4.16 mmol) of m-phenylenediamine (purified by washing it with acetone in a fritted filter funnel until colorless crystals were obtained) and 1.10 g (9.23 mmol) of 4-aminobenzocyclobutene was reacted in 120 ml acetic acid/60 ml toluene at 110° C. as described above. After the usual work-up, the crude product was dissolved in about 100 ml of methylene chloride and filtered through a bed of silica gel (50 g) on a fritted filtered funnel, washing with methylene chloride until the filtrate was almost colorless. Removal of the solvent from the yellow filtrate led to the isolation of the desired product as a light tan microcrystalline solid. Yield: 3.20 g.

EXAMPLE 8

Preparation of Intimate Bis-2,2 (N-4-benzocyclobutenyl phthalimido) hexafluoropropane and 1,1'-(Methylene di-4-,1-phenylene) bis-maleimide mixtures 1,1'-(Methylene di-4,1-phenylene)bis-maleimide was purchased and purified by passing through its $CH_2Cl_2$ solution through a bed of $SiO_2$ followed by subsequent rotary evaporation. Calc. for $C_{21}H_{14}N_2O_4$: 70.38% C, 3.94% H, 7.82% N. Found: 69.95% C, 3.99% H, 7.65% N.

0.1709 g(1.669×10$^{-4}$ mol) of Bis-2-2(N-4-benzocyclobutenyl phthalimido) hexafluoropropane and 0.0523 g(1.675×10$^{-4}$ mol) of 1,1'-(Methylene di-4,1-phenylene)bis-maleimide were dissolved completely in about 8 ml of $CH_2Cl_2$. The resultant solution was slowly evaporated to dryness with the assistance of a heat-gun. The mixture was then dried in an oven at 90° C. in vacuo for 48 hrs.

Having described the invention in detail and by reference to preferred embodiments thereof, it will be apparent that modifications and variations are possible without departing from the scope of the invention defined in the appended claims.

What is claimed is:

1. A compound of the formula

where R is divalent linking group.

2. The compound of claim 1 wherein said compound is represented by the formula

where R is a divalvent linking group.

3. The compound of claim 2 wherein said divalent linking group is an aromatic divalent linking group.

4. The compound of claim 2 wherein R is selected from the group consisting of —C(CF$_3$)$_2$—, —C(CH$_3$)$_2$—, —CH$_2$—, —O—, —S—, —CO— and —SO$_2$—, or R represents a direct bond.

5. The compound of claim 3 wherein R is represented by the formula

where W is selected from the group consisting of —C(CF$_3$)$_2$—, —C(CH$_3$)$_2$—, —CH$_2$—, —O—, —S—, —CO— and —SO$_2$—, or R represents a direct bond.

6. The compound of claim 3 wherein R is represented by the formula

where X is selected from the group consisting of —C(CF$_3$)$_2$—, —C(CH$_3$)$_2$—, —CH$_2$—, —O—, —S—, —CO— and —SO$_2$—, or R represents a direct bond.

7. The compound of claim 3 wherein R is represented by the formula where

R' is selected from the group consisting of —C(CF$_3$)$_2$—, —C(CH$_3$)$_2$—, —CH$_2$—, —O—, —S—, —CO— and —SO$_2$—, or R represents a direct bond, n is 1 to 4, and Ar is selected from the group consisting of a meta phenylene group, a para phenylene group, and the formula where X is selected from the group consisting of —C(CF$_3$)$_2$—, —C(CH$_3$)$_2$—, —CH$_2$—, —O—, —S—, —CO— and —SO$_2$—, or R represents a direct bond.

8. The compound of claim 4 wherein R is —C(CF$_3$)$_2$—.

9. The compound of claim 5 wherein W is —C(CF$_3$)$_2$—.

10. The compound of claim 5 wherein W is —SO$_2$—.

* * * * *